US005445143A

United States Patent [19]

Sims

[11] Patent Number: 5,445,143

[45] Date of Patent: Aug. 29, 1995

[54] HUMIDIFIER WITH DUAL FLOAT VALVES

[75] Inventor: David J. Sims, Auckland, New Zealand

[73] Assignee: Fisher & Paykel Limited, Auckland, New Zealand

[21] Appl. No.: 125,599

[22] Filed: Sep. 23, 1993

[30] Foreign Application Priority Data

Sep. 23, 1992 [NZ] New Zealand ........................ 244454

[51] Int. Cl.$^6$ .................... A61M 16/14; A61M 16/16; A61M 16/18; A61M 16/20

[52] U.S. Cl. ............................... 128/203.26; 137/423; 137/613; 251/210

[58] Field of Search ....................... 128/203.16, 204.14, 128/200.14, 203.12, 203.26; 137/423, 434, 451, 613, 329.01, 329.06, 442, 444, 411, 443 H; 261/139, DIG. 68; 251/210

[56] References Cited

U.S. PATENT DOCUMENTS

| | | | |
|---|---|---|---|
| 2,460,011 | 6/1949 | Hungerford, Jr. et al. | 137/423 |
| 3,049,144 | 8/1962 | Oleskow | 137/451 |
| 4,051,205 | 9/1977 | Grant | 261/70 |
| 4,352,371 | 10/1982 | Walters | 137/414 |
| 4,529,002 | 7/1985 | Jacobson | 137/414 |
| 4,529,867 | 7/1985 | Velnosky et al. | 219/274 |
| 4,913,140 | 4/1990 | Orec et al. | 128/203.16 |
| 5,010,915 | 4/1991 | Johnson et al. | 137/423 |

FOREIGN PATENT DOCUMENTS

| | | | |
|---|---|---|---|
| 424785 | 9/1947 | Italy | 137/423 |
| 522896 | 4/1955 | Italy | 137/423 |

*Primary Examiner*—Edgar S. Burr
*Assistant Examiner*—William J. Deane, Jr.
*Attorney, Agent, or Firm*—Trexler, Bushnell, Giangiorgi & Blackstone, Ltd.

[57] ABSTRACT

A humidification chamber for a respiratory humidifier water is maintained by the use of floats which actuate valves to control the passage of water through a water inlet. Two floats are each provided with actuating mechanisms to separately control the respective valve members. The separate valve members are covered by an elastomeric moulding which couples the valve members and provides a seal. The valves are co-axially aligned and the system provides improved safety by allowing for reliable operation in the case where one of the floats fails. An alternative embodiment of the dual valve construction is also disclosed.

10 Claims, 5 Drawing Sheets

HUMIDIFIER WITH DUAL FLOAT VALVES

BACKGROUND OF THE INVENTION

1. Field of the Invention

This invention relates to float valve systems and in particular but not solely float valve systems for respiratory humidification systems.

2. Description of the Prior Art

A respiratory humidification system includes a humidifier which is supplied with liquid water flow and a flow of gases (for example air including oxygen or an anaesthetic gas). The aim of the humidifier is to combine some of the water in the form of water vapour with the gas, thus raising the level of humidity of the gases and making it easier for a patient in a hospital or someone else in need of such gases to inhale them.

A humidifier in which the gases absorb water vapour from water or a water laden surface usually comprises a humidification chamber containing water and a heater base used to evaporate the water. A crucial aspect of respiratory humidifiers is in the control of the liquid water flow. It is imperative that liquid water not be allowed to pass directly to the patient for obvious reasons. Therefore, within the humidification chamber water valves are commonly used in various configurations to regulate the water flow.

Some prior an water valve mechanisms have been of a single valve type, configured with actuating means in order to stop the water entering the humidification chamber. An example is described in our U.S. Pat. No. 4,913,140. A solitary valve may give rise to difficulties in regard to reliability, as a problem with, for example, the valve seal or the actuating mechanism may cause overfilling. For this reason, prior respiratory humidification systems have introduced double valve mechanisms in a bid to increase reliability and thus the safety of the humidifier. An example is U.S. Pat. No. 4,529,867 to Veinosky et al. The double water valve mechanism described by Velnosky however, does not attempt to halt the flow of liquid water but merely to direct it elsewhere. A double valve configuration is disclosed in the aforesaid U.S. Pat. No. 4,913,140.

It is, therefore, an object of the present invention to provide a float valve and/or a respiratory humidifier which provides the public with a useful choice.

BRIEF SUMMARY OF THE INVENTION

Accordingly the invention consists in a float valve system for controlling the level of liquid in a chamber comprising a valve body having an inlet for coupling to a liquid supply conduit and an outlet adapted to communicate with said chamber. The float valve system also comprises a first valve seat formed in said body through which liquid must pass to reach said outlet and a second valve seat formed in said body located downstream of the first valve seat, through which liquid must pass to reach the outlet. The first and second floats being adapted to be disposed within the chamber.

A first valve member is activated by the first float so as to close onto the first valve seat on the first float assuming a position corresponding to a first predetermined level of liquid in said chamber. The float valve system also comprises a second valve member activated by the second float so as to close onto said second valve seat on the second float assuming a position corresponding to a second predetermined level of liquid in said chamber. The second predetermined level of liquid being higher than said first predetermined level of liquid.

In a further aspect the invention consists in a respiratory humidifier including a heated water chamber through which gas to be humidified is passed and a float valve system for controlling the level of water in the heated water chamber. The float valve system comprises a valve body mounted in the wall of said chamber having an inlet for coupling to a water supply conduit and an outlet opening into the chamber and a first valve seat formed in said body through which water must pass to reach the outlet. The float valve system also comprises a second valve seat formed in said body through which water must pass to reach the outlet, located downstream of said first valve seat. First and second floats are disposed within the chamber and a first valve member is activated by the first float so as to close onto the first valve seat on the first float assuming a position corresponding to a first predetermined level of water in the chamber.

A second valve member is activated by said second float so as to close onto the second valve seat on the second float assuming a position corresponding to a second predetermined level of water in said chamber, the second predetermined level of water being higher than the first predetermined level of liquid.

BRIEF DESCRIPTION OF THE DRAWINGS

The invention consists in the foregoing and also envisages constructions of which the following gives examples.

Preferred forms of the present invention will now be described with reference to the accompanying drawings in which:

FIG. 4: Both valves open

FIG. 5: Primary valve closed, secondary valve open

FIG. 6: Both valves closed

FIG. 7: Primary valve open, secondary valve closed

DETAILED DESCRIPTION OF THE PREFERRED EMBODIMENT

Figure 1:
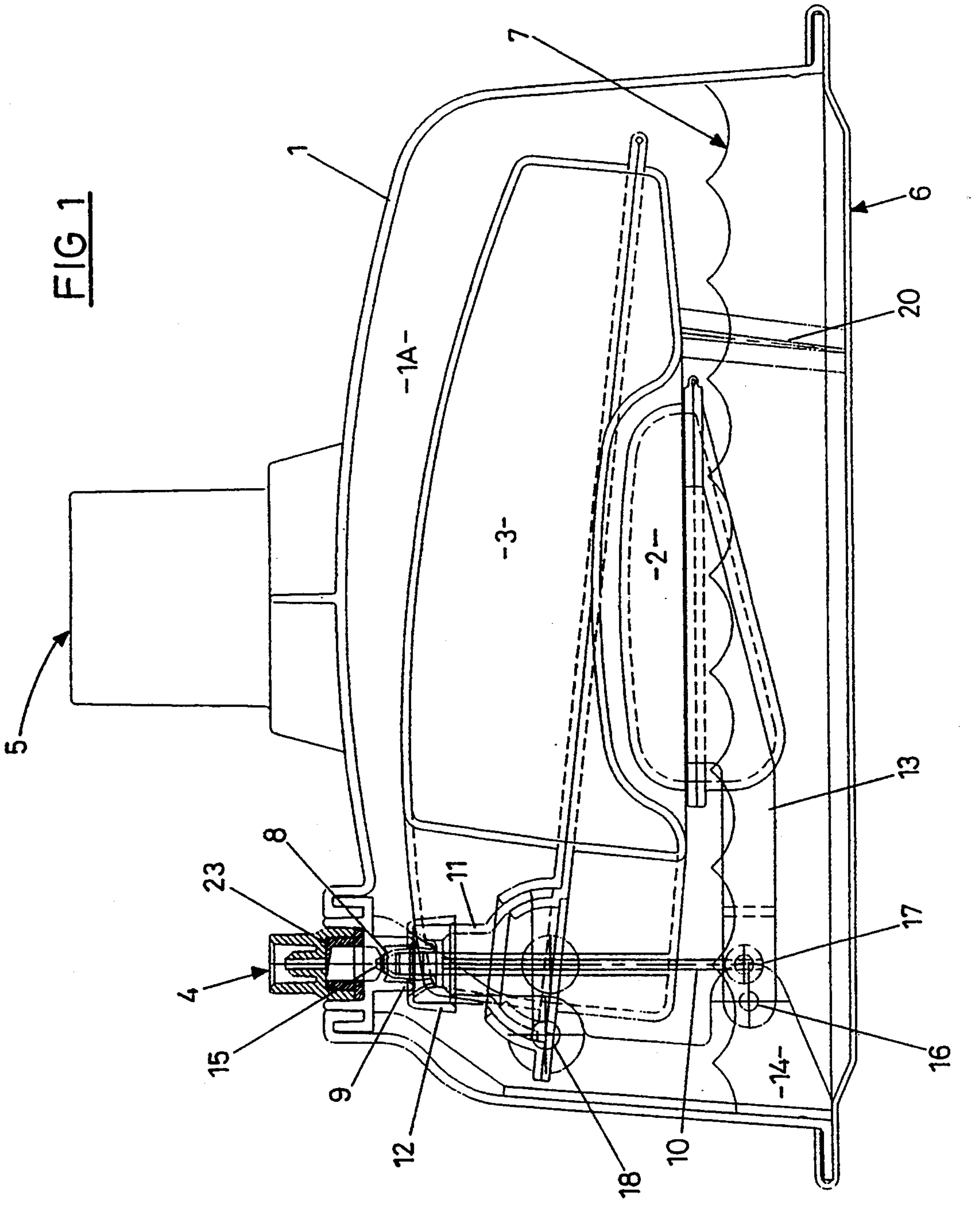
FIG. 1 is a cross-sectional elevation of a humidifier chamber incorporating the valve system of the present invention showing a normal water level.
Figure 2:
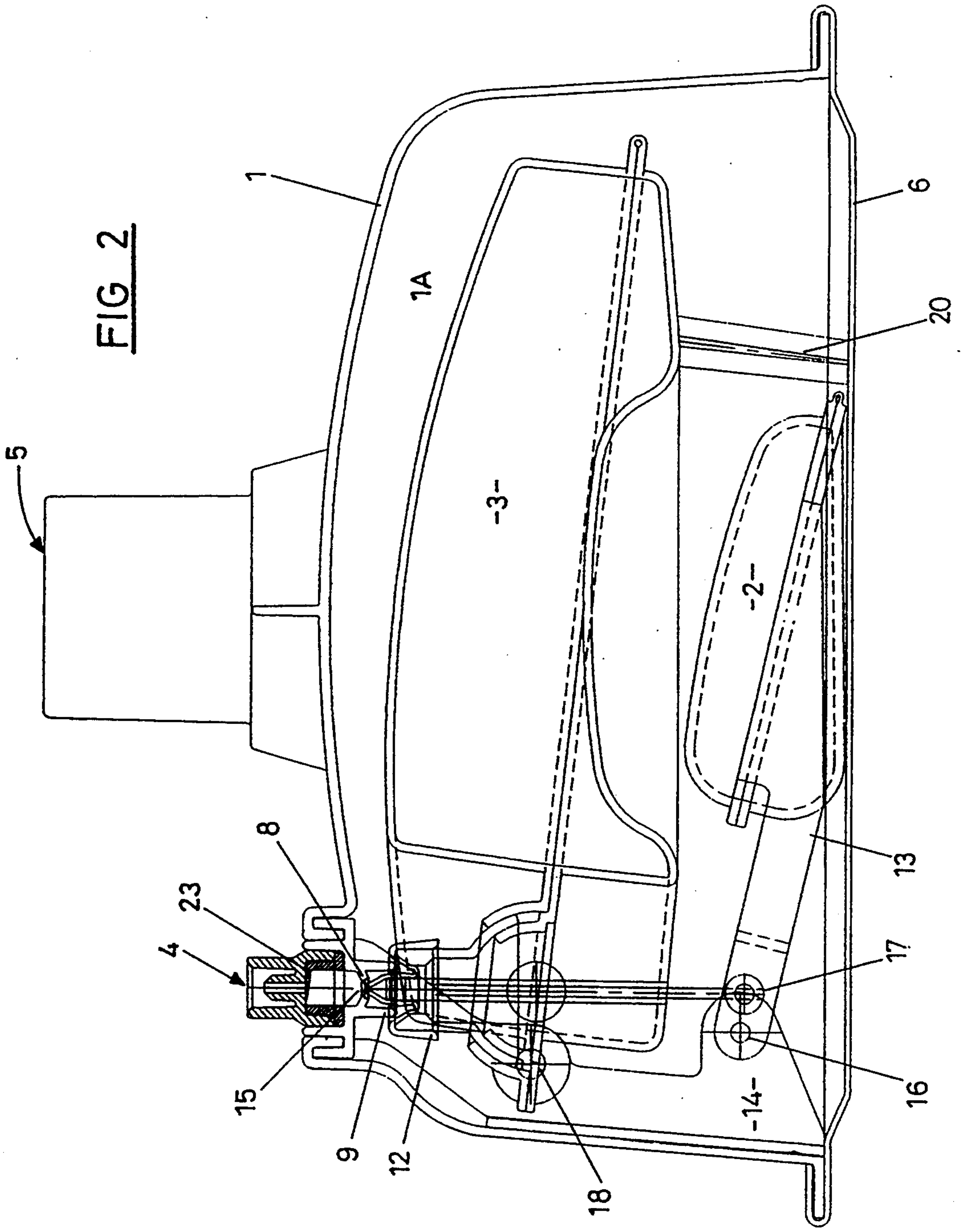
FIG. 2 shows the humidifier chamber of FIG. 1 devoid of liquid water.
Figure 3:
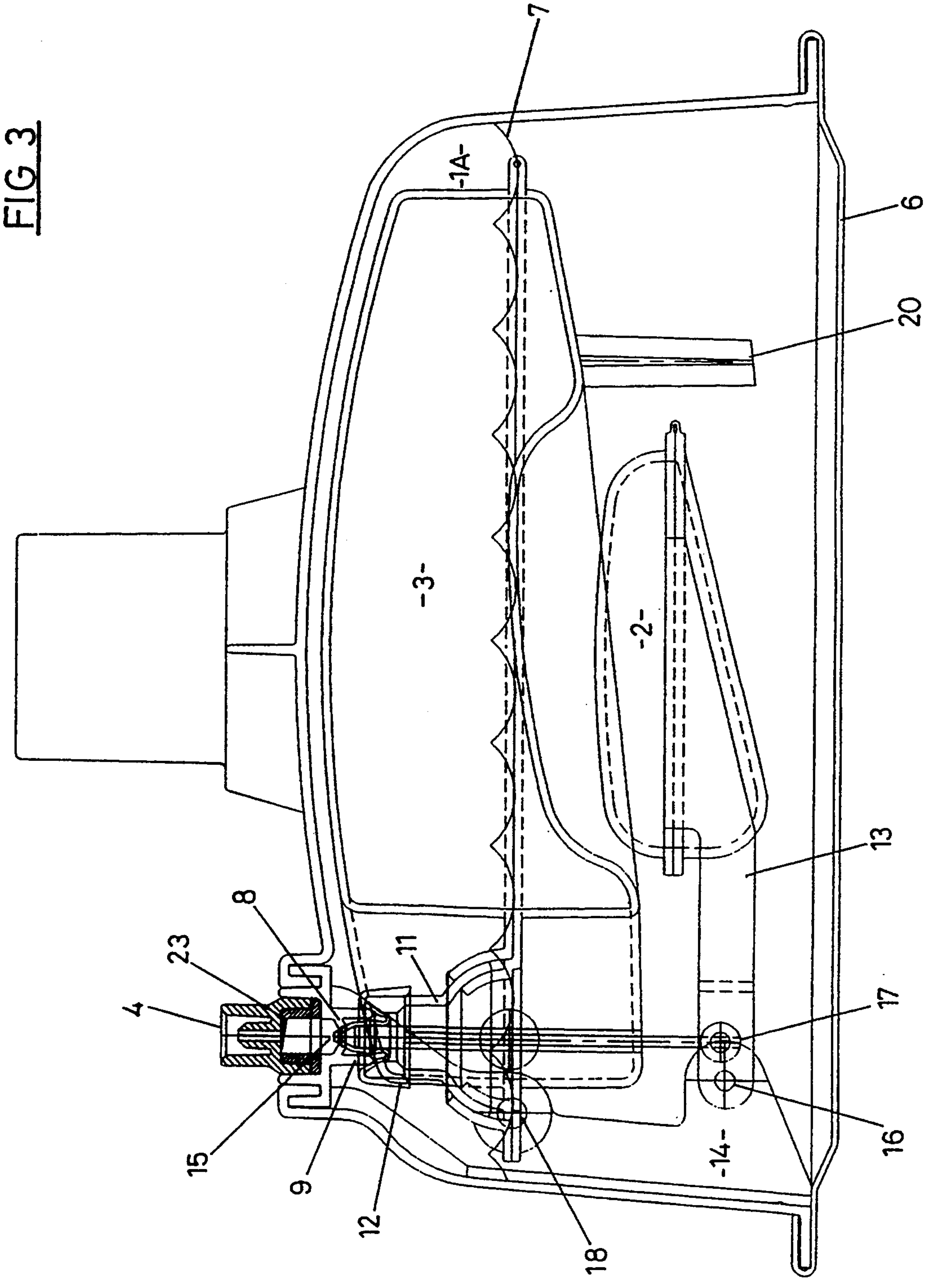
FIG. 3 shows the humidifier chamber of FIG. 1 in which the primary shut off system has failed and the secondary system is controlling the liquid water level.
Figure 9:
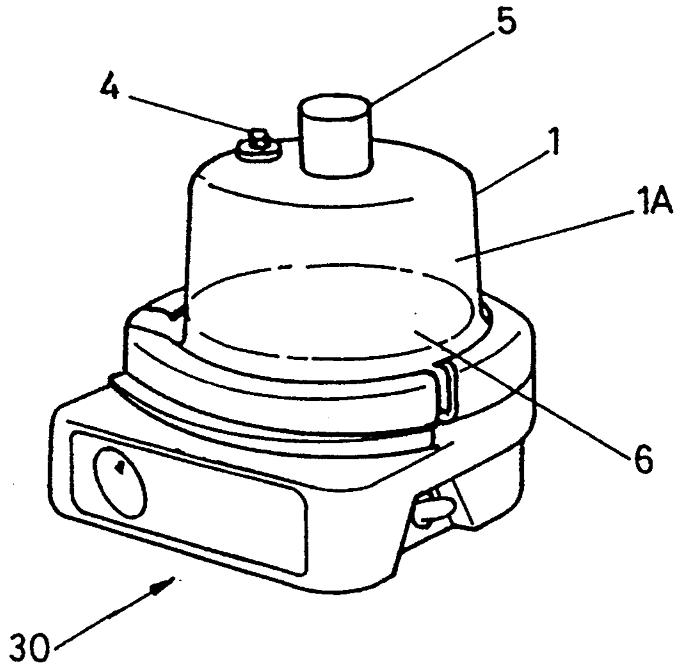
FIG. 9 shows a respiratory humidifier including the valve system of FIG. 7.

With reference to FIGS. 1, 2 and 3, a humidification chamber 1A for fitting to a respiratory humidifier 30, for example as shown in FIG. 9, is made up of a preferably transparent humidification chamber molding 1 which is sealed to an aluminum heat transfer base 6 by a process which forms an annular lip around the humidification chamber. An external water reservoir (not shown) supplies liquid water to the humidification chamber 1A through a water inlet 4 in use. The humidification chamber 1A contains water in both liquid and vapour phases and is similar in construction to that disclosed in U.S. Pat. No. 4,913,140 and should be operated with the base 6 in a substantially horizontal plane.

Liquid water enters the humidification chamber 1A through inlet 4 and rises against the walls of the humidification chamber to a level dependent on the amount of water allowed to enter the chamber. A double float arrangement is shown within the humidification chamber 1A made up of two independent air filled, sealed plastic moldings which are able to rise and fall with the water level. The operation of this double float valve system is described below A first or primary float 2 is fabricated to include an arm 13 which is connected by a pivot 16 to a hinge moulding 14 which is further bonded to the humidification chamber molding 1. A second or secondary float 3 operates in conjunction with primary float 2 as a safety improvement system. The secondary float 3 is pivoted at 18 by a connection with the hinge molding 14. The lower surface of secondary float 3 is provided with a foot 20 positioned near the end of the secondary float 3 furthest from the pivot 18 in order that the secondary float 3 may not fall to a position below a predetermined height. The humidification chamber 1A is further equipped with a gases inlet (not shown) and a gases outlet 5. In the process of humidification, the base 6 of the humidification chamber 1A is provided with heat from a controlled source of heat (not shown), causing vapour to rise from the surface of the liquid water which mixes with the gases (for example, air including oxygen or anaesthetic gas).

The primary float 2 and secondary float 3, as shown, are preferably located concentrically both within the humidification chamber 1A and relative to each other. This arrangement is such that upon the humidification chamber 1A being tilted from a substantially horizontal plane, water level changes adjacent to the gases inlet (not shown) and gases outlet 5 are miniraised. The secondary float 3 is physically larger in size than the primary float 2 and occupies a significant volume of chamber 1A. The reason for the relative volumes and shapes of the chamber and floats is to minimize the compressible volume of the humidification chamber 1A and also so that gases in the humidification chamber 1A may be directed to effect more efficient humidification. In addition the larger size of the secondary float 3 is useful in giving an increased closing force of the valve molding 12 onto the valve seat 9. It is to be understood that the floats 2 and 3 could be the same size or be located beside each other in the humidification chamber.

The water inlet 4 incorporates a two stage valve arrangement which, in use, is substantially oriented in the vertical plane. The section of the water inlet 4 facing the valve mechanism is specially constructed with a primary valve seat 8 and the secondary annular valve seat 9. The valve actuating mechanism comprises an inner push rod 10 within a preferably co-axial outer cylindrical push tube 11, both capable of moving freely and independently within limits. The end of the push rod 10 facing the water inlet 4 is tapered to a blunt point 15 and covered by an elastomeric valve molding 12, manufactured in such a shape as to also fit snugly over the rim of the outer push tube 11, thus coupling the push tube 11 to the push rod 10 in a floating connection. The elastomeric valve molding 12 is made of material which is very supple but strong, for example, the material sold under the trade mark KRATON as supplied by Shell Corporation, or a silicone rubber as supplied by Dow Corning (Medical) would be suitable.

The water inlet 4 may also include a flexible membrane 23 which operates as a non-return valve to prevent water or gas travelling in a direction from the humidification chamber 1A to the water inlet 4.

The push rod 10 of the valve mechanism has, at its lower end, a pivot 17 to the arm 13 of the primary float 2, near the connection 16 of the hinge molding 14 and the arm 13. The push tube 11 is pivoted at its lower end by a hollow ball joint which attaches it to the secondary float 3 near the connection 18 of the hinge molding 14 and the secondary float 3.

With reference to FIGS. 4, 5, 6 and 7, the arrangement and operation of the valves according to the present invention will now be described.

Figure 4:
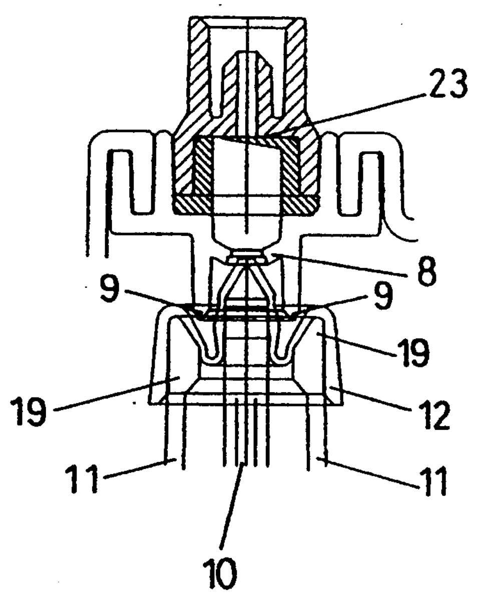
FIGS. 4, 5, 6 and 7 show the valve system of FIG. 1 in the following modes of operation.
Figure 5:
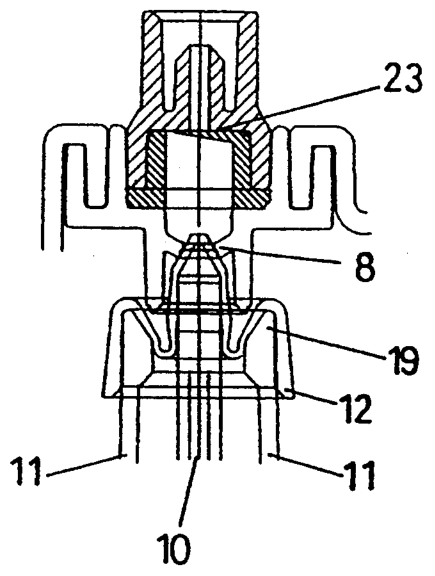

An inner push rod 10 is surrounded cylindrically by an outer push tube 11, both of which can move independently but are loosely coupled by an elastomeric vane molding 12 at their respective ends facing the water inlet 4. The valve molding 12 forms a seal with either, or both, of the valve seats 8 and 9. Both the push rod 10 and the push tube 11 move in substantially a vertical plane, the push rod 10 being controlled by the actions of the primary float 2 and the push tube 11 displaced in reaction to movement of the secondary float 3. In FIG. 4 it can be seen that a gap exists between the valve molding 12 at the region covering the push tube shoulders 19 and the secondary valve seat 9. Also, a gap exists between the valve molding 12 in the region covering the tapered part of the push rod 10 and the primary valve seat 8. Thus, FIG. 4 displays a state in which both valves are open so that water may flow into the humidification chamber 1A from the external reservoir. The float arrangement giving rise to this eventuality is illustrated in FIG. 2 where both floats are lowered and there is substantially no liquid water in humidification chamber 1A. The same configuration of valves is occasionally found in the situation described by FIG. 1 in which the primary float 2 is actively controlling the water level by periodically raising the push rod 10 to form a seal between the primary valve seat 8 and the portion of valve molding 12 covering the tapered section of push rod 10. This configuration is shown in FIG. 5 for an instant in time when the primary valve is closed and the secondary valve is open. In this situation no water will flow into the humidification chamber 1A.

Figure 6:
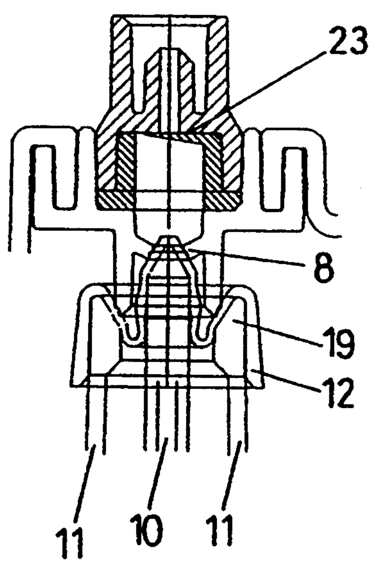
Figure 7:
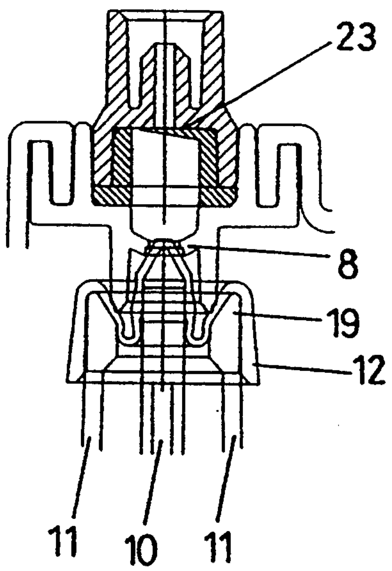

If a situation were to occur as depicted in FIG. 3 where the primary valve has not functioned (for example there may be a leak in the seal), the water level will be significantly higher so that the primary float 2 will be substantially or fully submerged and the secondary float 3 will come into play. It is vital that the water level should not increase to a level whereby liquid water would be forced out of the gases outlet 5 and into the patient. Therefore, due to the rising water level, the secondary float 3 will raise the push tube causing the region of the valve molding over the shoulder 19 of the push tube 11 to form a seal with the secondary valve seat 9. The valve positions for this occurrence are shown in FIG. 6.

There may also arise a situation where the primary float 2 may fail and not close the primary valve (for example, if float 2 develops a hole). In this situation, the water level will rise above the primary float (as in FIG. 3) until the secondary float is activated. The secondary float will close the secondary valve and then actively control the water level within the humidification chamber 1A. The valve positions arising from this sequence of events may be seen in FIG. 7. Thus although the primary valve may have realfunctioned, the secondary valve can, when needed, be relied upon to close and then open again if necessary due to an inadequate amount of liquid water in the humidification chamber 1A.

Figure 8:
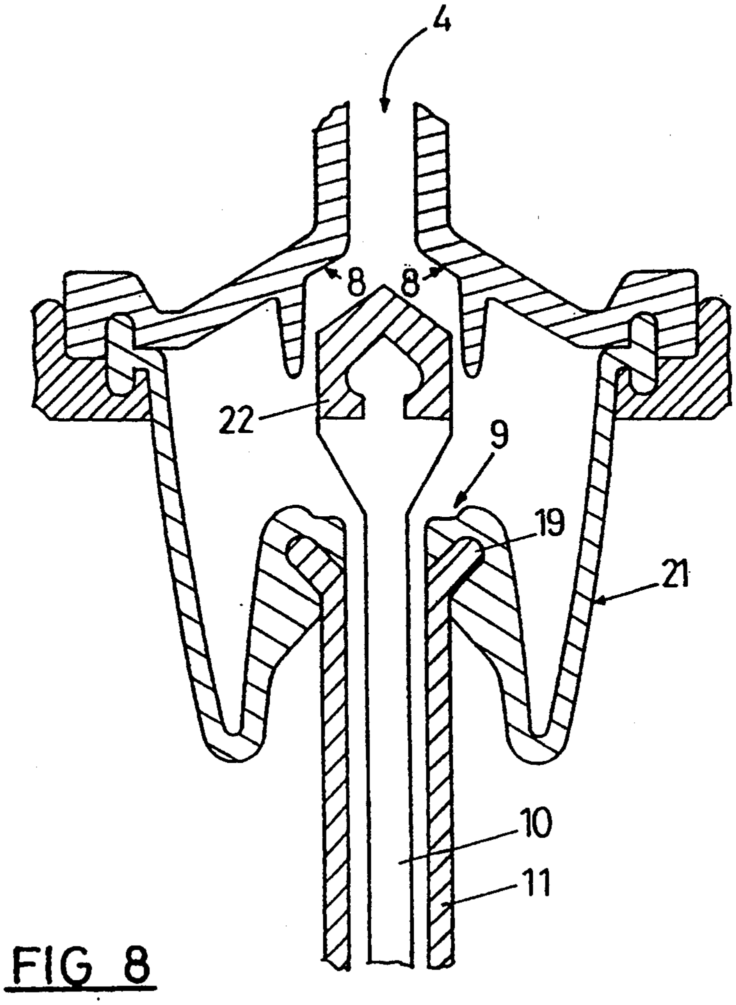
FIG. 8 is an alternative embodiment of the present invention.

An alternative preferable embodiment of the present invention is shown in FIG. 8. It can be seen that the push rod 10 and the push tube 11 are incorporated in the water inlet 4 as before. The primary float 2 and secondary float 3 are not shown but are connected to the two valve members as previously described. The push rod 10 and the push tube 11 are not coupled by an elastomeric valve molding but instead there is now an elastomeric primary valve molding 22 and a separate elastomeric secondary valve molding 21. In this embodiment, water flows into the chamber from the valve cavity and down the space between the push rod and the push tube.

The operation of the valve mechanism of this alternative preferred embodiment will now be described. Upon the primary float 2 rising in response to an increase in the water level of the humidification chamber 1A, the push rod 10 will be forced to rise. On occasion, the push rod 10 may rise sufficiently to cause the elastomeric primary valve molding 22 to come into contact with the primary valve seat 8. This would constitute closure of the primary valve, causing a stoppage to the flow of water from the external reservoir (not shown) to the humidification chamber 1A.

The secondary valve mechanism encompasses a secondary valve seat 9 which is formed as part of the push tube 11 with its attached elastomeric secondary valve molding 21. If circumstances were to arise in which the secondary float 3 was to rise sufficiently in response to an increase in water level in the humidification chamber 1A to allow the region of the valve seat 9 over the shoulders of the push tube 11 to contact the region of push rod 10 adjacent valve seat 9, then the secondary valve would be closed and no water would flow into the humidification chamber 1A from the external reservoir (not shown).

The float valve system according to at least the preferred form of the invention has the advantage of providing a safety factor in controlling water flow into a humidification chamber. Should the first float valve fail, observation through a transparent chamber wall will show this malfunction, but even of such observation is delayed, the second float valve should adequately take over control.

We claim:

1. A float valve system for controlling the level of liquid in a chamber comprising:

a valve body having an inlet for coupling to a liquid supply conduit and an outlet adapted to communicate with said chamber, a first valve seat formed in said body through which liquid must pass to reach said outlet, a second valve seat formed in said body located downstream of said first valve seat, through which liquid must pass to reach said outlet, first and second floats adapted to be disposed within said chamber, a first valve member actuated by said first float so as to close onto said first valve seat upon the first float assuming a position corresponding to a first predetermined level of liquid in said chamber, a second valve member actuated by said second float so as to close onto said second valve seat upon the second float assuming a position corresponding to a second predetermined level of liquid in said chamber, said second predetermined level of liquid being higher than said first predetermined level of liquid, a cylindrical actuating member connected to said second valve member in order to control displacement of said second valve member in response to said second float, an inner actuating member connected to said first valve member in order to control displacement of said first valve member in response to said first float, said inner actuating member being disposed within said cylindrical actuating member, said cylindrical actuating member and said inner actuating member independently connecting said first and second floats to respective valve members, and operable to allow free relative movement between said first and second valve members.

2. A float valve system as claimed in claim 1 wherein said valve seats are coaxial.

3. A float valve system as claimed in claim 1 said inner actuating member is disposed coaxially within said cylindrical actuating member.

4. A float valve system as claimed in claim 1 or claim 2 wherein said first and second valve members are formed from a common unitary elastomeric membrane, the central region of which forms the first valve member and the concentric outer region of which forms the second valve member.

5. A float valve system as claimed in claim 2 or claim 3 wherein said first and second valve members are formed from a common unitary elastomeric membrane, the central region of which forms the first valve member and the concentric outer region of which forms the second valve member and wherein said elastomeric membrane is fitted about the adjacent ends of said inner and cylindrical actuating members and the valve members are each closed by said members pushing respective regions of said membrane into sealing engagement with said valve seats.

6. A respiratory humidifier including a water chamber adapted to be heated through which gas to be humidified is passed and a float valve system for controlling the level of water in said water chamber, said float valve system comprising:

a valve body mounted in the wall of said chamber having an inlet for coupling to a water supply conduit and an outlet opening into said chamber, a first valve seat formed in said body through which water must pass to reach said outlet, a second valve seat formed in said body through which water must pass to reach said outlet, located downstream of said first valve seat, first and second floats disposed within said chamber, a first valve member actuated by said first float so as to close onto said first valve seat upon the first float assuming a position corresponding to a first predetermined level of water in said chamber, a second valve member actuated by said second float so as to close onto said second valve seat upon the second float assuming a position corresponding to a second predetermined level of water in said chamber, said second predetermined level of water being higher than said first predetermined level of liquid, a cylindrical actuating member connected to said second valve member in order to control displacement of said second valve member in response to said second float, an inner actuating member connected to said first valve member in order to control displacement of said first valve member in response to said first float, said inner actuating member being disposed within said cylindrical actuating member, said cylindrical actuating member and said inner actuating member independently connecting said first and second floats to respective valve members, and operable to allow free

7. A respiratory humidifier as claimed in claim 6 wherein said valve seats are coaxial.

8. A respiratory humidifier as claimed in claim 6 wherein said inner actuating member is disposed coaxially within said cylindrical actuating member relative movement between said first and second valve members.

9. A respiratory humidifier as claimed in either claims 6 or 7 wherein said first and second valve members are formed from a common unitary elastomeric membrane, the central region of which forms the first valve member and the concentric outer region of which forms the second valve member.

10. A respiratory humidifier as claimed in claim 7 or claim 8 wherein said first and second valve members are formed from a common unitary elastomeric membrane, the central region of which forms the first valve member and the concentric outer region of which forms the second valve member and wherein said elastomeric membrane is fitted about the adjacent ends of said inner and cylindrical actuating members and the valve members are each closed by said members pushing respective regions of said membrane into sealing engagement with said valve seats.

* * * * *

UNITED STATES PATENT AND TRADEMARK OFFICE

CERTIFICATE OF CORRECTION

PATENT NO. : 5,445,143

DATED : August 29, 1995

INVENTOR(S) : David J. Sims

It is certified that error appears in the above-indentified patent and that said Letters Patent is hereby corrected as shown below:

Column 1, Line 28 "prior an" should be -- prior art --

Column 1, Line 39 "Veinosky" should be -- Velnosky --

Column 3, Line 14 "moulding" should be -- molding --

Column 5, Line 1 "realfunctioned" should be -- malfunctioned--

Column 7, Line 11 please add after"to allow free"-- relative movement between said first and second valve members. --

Column 7, Lines 16, 17 and 18 "relative movement between said first and second valve members" should be deleted.

Signed and Sealed this

Twenty-eighth Day of November 1995

Attest:

BRUCE LEHMAN

Attesting Officer

*Commissioner of Patents and Trademarks*